United States Patent [19]

Schaefer

[11] Patent Number: 5,390,663
[45] Date of Patent: Feb. 21, 1995

[54] CANAL OBSTRUCTION REMOVER

[76] Inventor: Nicholas E. Schaefer, 29801 Fir Dr., Evergreen, Colo. 80439

[21] Appl. No.: 172,589

[22] Filed: Dec. 23, 1993

[51] Int. Cl.$^6$ .............................................. A61B 1/22
[52] U.S. Cl. ........................................ 128/9; 606/1; 606/106
[58] Field of Search ................ 606/1, 106; 128/4, 6, 128/9, 17–19

[56] References Cited

U.S. PATENT DOCUMENTS

| 944,830 | 12/1909 | Sussmann . | |
|---|---|---|---|
| 1,737,106 | 11/1929 | Campbell . | |
| 2,241,576 | 5/1941 | Barton | 46/152 |
| 2,331,732 | 10/1943 | Ryzmek . | |
| 2,498,692 | 2/1950 | Mains . | |
| 2,799,274 | 7/1957 | Eisenhut . | |
| 2,975,785 | 3/1961 | Sheldon | 128/6 |
| 3,060,972 | 10/1962 | Sheldon | 138/120 |
| 3,110,304 | 11/1963 | Hartman | 128/9 |
| 3,162,214 | 12/1964 | Bazinat | 138/120 |
| 3,266,059 | 8/1966 | Stelle | 3/12.3 |
| 3,557,780 | 1/1971 | Sato | 128/4 |
| 3,583,393 | 6/1971 | Takahashi | 128/4 |
| 3,626,946 | 12/1971 | Massey . | |
| 3,635,222 | 1/1972 | Robinson . | |
| 3,799,151 | 3/1974 | Fakaumi | 128/6 |
| 3,840,004 | 10/1974 | Heine | 128/9 |
| 3,948,251 | 4/1976 | Hosono | 128/4 |
| 4,006,738 | 12/1977 | Moore | 128/9 |
| 4,044,770 | 8/1977 | Ocel . | |
| 4,186,517 | 2/1980 | Kuhn | 46/119 |
| 4,198,960 | 9/1980 | Utsugi | 128/6 |
| 4,271,845 | 6/1981 | Chikashiga | 128/756 |
| 4,411,265 | 10/1983 | Eichenlaub . | |
| 4,469,100 | 9/1984 | Hardwick . | |
| 4,572,180 | 2/1986 | Deenadayalis . | |
| 4,785,796 | 11/1988 | Mattson | 129/9 |
| 4,840,176 | 8/1989 | Ohno . | |
| 4,873,965 | 10/1989 | Danieli | 128/6 |
| 5,038,755 | 8/1991 | Burgio | 128/9 |
| 5,057,114 | 10/1991 | Wittich | 606/127 |
| 5,074,867 | 12/1991 | Wilk | 606/128 |
| 5,108,406 | 4/1992 | Lee | 606/106 |
| 5,133,721 | 7/1992 | Angulo | 606/106 |
| 5,147,371 | 9/1992 | Washington | 606/127 |
| 5,171,233 | 12/1992 | Amplatz | 604/281 |

Primary Examiner—Stephen C. Pellegrino
Assistant Examiner—Glenn K. Dawson
Attorney, Agent, or Firm—Rick Martin

[57] ABSTRACT

An otoscopic ear speculum is improved to enable removal of substances or objects from the ear canal. Alternate embodiments can perform like functions in other body orifices. The ear speculum incorporates one or more protrusions that move independently of the body of the speculum.

In one embodiment, protrusions can be bent back towards the distal end of the speculum. Bending is accomplished by pulling a filament attached to the end of the protrusion. The filament may be pulled manually or with the aid of a trigger or a rotating knob.

When placed inside of, or extended from a tube, protrusion mechanisms may serve as a surgical tool. The surgical tool may be adapted to fit a variety of body orifices.

11 Claims, 17 Drawing Sheets

CANAL OBSTRUCTION REMOVER

CROSS REFERENCE PATENTS

The following U.S. Patents are incorporated herein by reference, U.S. Pat. No. 5,133,721 issued Jul. 28, 1992 to Angulo.

FIELD OF INVENTION

The present invention relates to an improved ear speculum having a bending tool and a general purpose medical tool for removing foreign objects.

BACKGROUND OF THE INVENTION

Often it is desirable to inspect the ear drum and the ear canal for evidence of infection, bulging, or simply for earwax which may plug the ear. In children foreign material such as cotton, tissue paper, or even small toy beads, for example, may be found to occlude the ear canal and thus necessitate removal.

Practitioners such as an ear, nose and throat (ENT) specialists routinely have specialized equipment such as binocular microscopes, head mirrors providing illumination, suction devices, irrigation, and other special devices at their disposal. Such devices are quite expensive, however, and may further require special skills for their use, or a second person to hold the patient's head during the procedure.

Practitioners have frequently carried out examinations of the ear canal with prior art otoscopes. If occluding matter was found, then the ear would be irrigated with warm water and other solvents. This dissolves or softens the occluding material to permit the removal thereof. Once the matter, such as wax, is softened by the irrigation fluid, it would often be removed manually with the aid of a metal curette having a head portion bowed to better fit the ear.

Examinations carried out in the foregoing manner using metal curettes could easily result in the abrasion of the tissues of the ear, especially when those tissues are wetted and softened by the irrigation fluid. Occasionally, even perforation of the ear drum could result. The risks involved in performing these procedures with equipment known in the art are even further increased when examining and treating small children. As is all too well known, children will cooperate minimally if at all, and are likely to become fearful and move about during the examination. Moreover, due to the noise and sensation of the curette within the ear, some children may develop vertigo and nausea during examination or treatment. Thus, these procedures are made quite complicated by the child's movements, and much time is required to complete the examination and the treatment.

The problems inherent in examining various sensitive orifices of the body have been recognized. Improved otoscopes and other ear cleaning devices have resulted. For example, U.S. Pat. No. 4,572,180 discloses a lighted ear canal curette instrument including a hand-held lighting member, a curette having an elongated handle and retaining members which telescopically receive both the handle member and the curette to secure the curette thereto. A magnification lens is hingedly attached to the lighting member to provide a view path as well as an optical path into the ear canal.

To avoid injuring the tissues of the ear, especially the ears of small children during the inspection and cleaning thereof, excellent visual access and support should be provided. This is especially important when the canal is made wet and particularly sensitive due to the softening effects of irrigating solutions or the like.

Below follows a brief synopsis of the most relevant prior art:

U.S. Pat No. 4,006,738 (1977) to Moore, et al. discloses the well known Welch Allyn, Inc. otoscope. It uses a halogen lamp positioned in the handle of the device. A bundle of optical fibers points the light into the viewing passage. Thus, there are no protuberances in the viewing passage.

U.S. Pat. No. 3,162,214 (1964) to Bazinet, Jr. discloses a bendable tube made up of a series of rings inside and outside of a tube. At least one pair of tensioning wires allows the tube to be bent by pulling on the periphery of the rings thereby compressing them. This device could conceivably be used for retraction, but it is more useful to house a fiber optics device. It is the closest art found. It does not teach a semi circular embodiment nor does it teach a combination with an otoscope. The cylindrical tube could not fit around a foreign body. It generally teaches a flexible cylindrical tube used for housing an instrument.

U.S. Pat. No. 3,799,151 (1974) to Fukaumi et al. discloses a fiber optic endoscope. A yieldably flexible main tube can be controllably bent by tensioning a pair of wires located in the opposite sides of the main tube. There is also a bendable tip portion having a second set of tensioning wires. In operation the doctor can choose to tension either or both sets of tensioning wires to bend the fiber optic tube to his choosing. Annular segments allow the controlled bending of the bendable tubes when the tensioning wires are tensioned. The tensioning of the wires shortens the length of the bendable tube. The annular segments allow a smooth bending of the bendable tube as the segments overlap. There is no teaching of retraction of foreign matter using this instrument.

U.S. Pat. No. 944,830 (1909) to Sussmann discloses a flexible gastroscope. A series of tubular links have peripheral channels for tensioning wires. Internal mirrors provide a viewing means.

U.S. Pat. No. 2,799,274 (1957) to Eisenhut discloses a veterinary evacuating probe. A pair of tensioning cables pass through the periphery of a series of articulating members. A magnet at the tip is used to detect and remove ferrous material from the stomach of a cow. Only movement in one plane is permitted.

U.S. Pat. No. 4,785,796 (1988) to Mattson discloses an otoscope with a flexible but not controllably bendable curette.

U.S. Pat. No. 4,572,180 (1986) to Deenadayalu discloses a lighted curette having a magnification lens.

U.S. Pat. No. 3,110,304 (1963) to Hartman discloses an ear speculum having a scooping spoon at the distal end. The spoon is manipulated to scoop out wax.

U.S. Pat. No. 5,133,721 (1992) to Angulo discloses an electric powered shape - memory - effect alloy used as a device for removing foreign objects. A wire tip of a curette bends either alone or in conjunction with a second member to form a tweezer. The device allows insertion of the tip past a foreign object and then the tip bends around the object for removal. The tip must then be manually bent back into shape. The device is a relatively costly device not suited for use as a disposable.

U.S. Pat. No. 4,198,960 (1980) to Utsugi discloses a foreign matter removal device having a sheath. The sheath houses a plurality of trapping wires forming a distal net. The wires are manipulated to snare the foreign matter.

U.S. Pat. No. 4,271,845 (1981) to Chikashige et al. discloses a bending device for medical instruments. A series of coarsely wound segments bend when a central tensioning wire is pulled. The device has a cylindrical cross section.

Of all the above inventions Hartman approaches the closest to an ideal solution. Hartman teaches a projection integrally formed on the distal end of a disposable plastic speculum. The projection is designed to remove the obstructing cerumen by rotational, hooking or scooping motion of the speculum, while the cerumen and the ear canal are under direct visual observation. The removal of cerumen under direct visual observation minimizes any risk of injury to the ear canal or tympanic membrane.

However, the problem persists of causing great discomfort in the patient by the rotational, hooking or scooping motion of the speculum. The speculum will rub against the ear canal with these motions. If infection or swelling exists, then the rubbing will cause great discomfort especially in children.

The present invention in its preferred embodiment improves on Hartman's invention by allowing the projection to be bent under the physician's control. Even more importantly the projection is shaped so as to fit between a foreign object and a body canal. The physician can bend the improved projection by using the index finger of the hand holding the otoscope. A mechanical linkage is made up of a control knob, a pair of guide filaments and a flexible projection. The flexible projection can controllably scrape the cerumen without moving the speculum. Alternatively the projection can be inserted past the cerumen or other foreign matter and then be bent and then extract the foreign matter. Thus, the patient discomfort is eliminated and the risk of causing patient movement is reduced considerably.

SUMMARY OF THE INVENTION

Before proceeding with a description of the present invention a brief glossary of the common terms of the art is presented below:

BRIEF GLOSSARY shank - a narrow part of various devices, as a tool, bolt, etc., connecting the end by which the object is held or moved with the end which sets upon another object.

otoscope - an instrument for examining the external canal and tympanic membrane of the ear.

speculum - an instrument for rendering a part accessible to observation as by enlarging an orifice.

curette - a scoop-shaped surgical instrument for removing diseased tissue from body cavities.

cerumen - a yellowish wax-like secretion from certain glands in the external auditory canal - also called earwax.

endoscope - a slender, tubular instrument, used to examine the interior of a body cavity.

articulate - to unite by a joint or joints.

lumen - canal, duct, or cavity of a tubular organ.

The present invention differs from the prior art by providing a projection having an axially curved and narrow profile. This curved and narrow profile can be made to conform to the dimensions of the body canal in which it is to be inserted. This curved and narrow profile looks substantially like a circular segment when viewed from the front. When a foreign object such as a bead is blocking a canal such as a child's nasal passage, then a projection shaped like a circular segment can be readily passed by the foreign object.

Once past the foreign object the projection can be controllably bent by inexpensive mechanical means. The preferred embodiment uses a length of plastic having a channel along each side. Each channel houses a tensioning filament. The tensioning filament is threaded through these peripheral channels and around a channel in the distal end of the projection or fastened thereto. The ends of the tensioning filament extend from the proximal end of the length of plastic. When these ends are simultaneously pulled they controllably bend the length of plastic much like the motion of the human finger.

In operation this controlled bending of the curved, narrow projection hooks around a foreign object. The foreign object is then removed from the canal.

For the removal of cerumen from the ear it is also possible to merely scratch off pieces of the cerumen directly from the front of the mass. It may not be necessary to pass the projection past the cerumen until the cerumen has been whittled down to size one piece at a time. All of this delicate removal of cerumen or foreign matter is possible without laterally moving the speculum against the body canal.

Other embodiments of the present invention include either a rotating knob or a push/pull trigger actuating the pull on the tensioning filaments.

A generic embodiment adds a cylindrical tube around the projection. The tube can house a fiber optic cable and/or surgical tools in addition to the curved, narrow projection. This generic embodiment can be used for surgical procedures involving the removal of foreign matter from body canals. A second pair of tensioning filaments may be provided to allow a direct pull on the tip of the projection to better secure a foreign object.

An alternate embodiment provides a scissor-like or forcept like projection from the distal end of the speculum. The projection is made of two cooperating spoon halves. This embodiment can be used to scratch away or grasp at a piece of cerumen or foreign object such as paper.

Finally, an alternative embodiment of the projection has the tensioning filaments fastened only to the tip of the projection rather than through channels. This embodiment enables the physician to positively grab a foreign object such as a bead. The physician may choose to use this embodiment for clearing foreign objects from the nasal passages.

The primary object of the present invention is to provide a curved, narrow bendable projection for the removal of foreign objects from a body canal.

Another object of the present invention is to provide a combination of the curved, narrow bendable projection with a disposable ear speculum.

Another object of the present invention is to provide a one finger mechanical actuation of the combination device from the otoscope upon which it is mounted.

Another object of the present invention is to provide a generic surgical tool having a cylindrical tube housing the curved, narrow projection.

Another object of the present invention is to provide a pair of tensioning filaments peripheral to the curved, narrow bendable projection for providing a bending torque.

Another object of the present invention is to provide one or more tensioning filaments directly attached to the tip of the curved, narrow projection to provide a bending and grasping torque.

Another object of the present invention is to provide a movable spoon half projection on the tip of an ear speculum for scraping out cerumen.

Other objects of this invention will appear from the following description and appended claims, referenced being had to the accompanying drawings forming a part of this specification wherein like reference characters designate corresponding parts in the several views.

BRIEF DESCRIPTION OF THE DRAWINGS

FIG. 14(a) shows the distal end of the shank enclosed within its cylindrical tube.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENTS

Figures 1, 2:
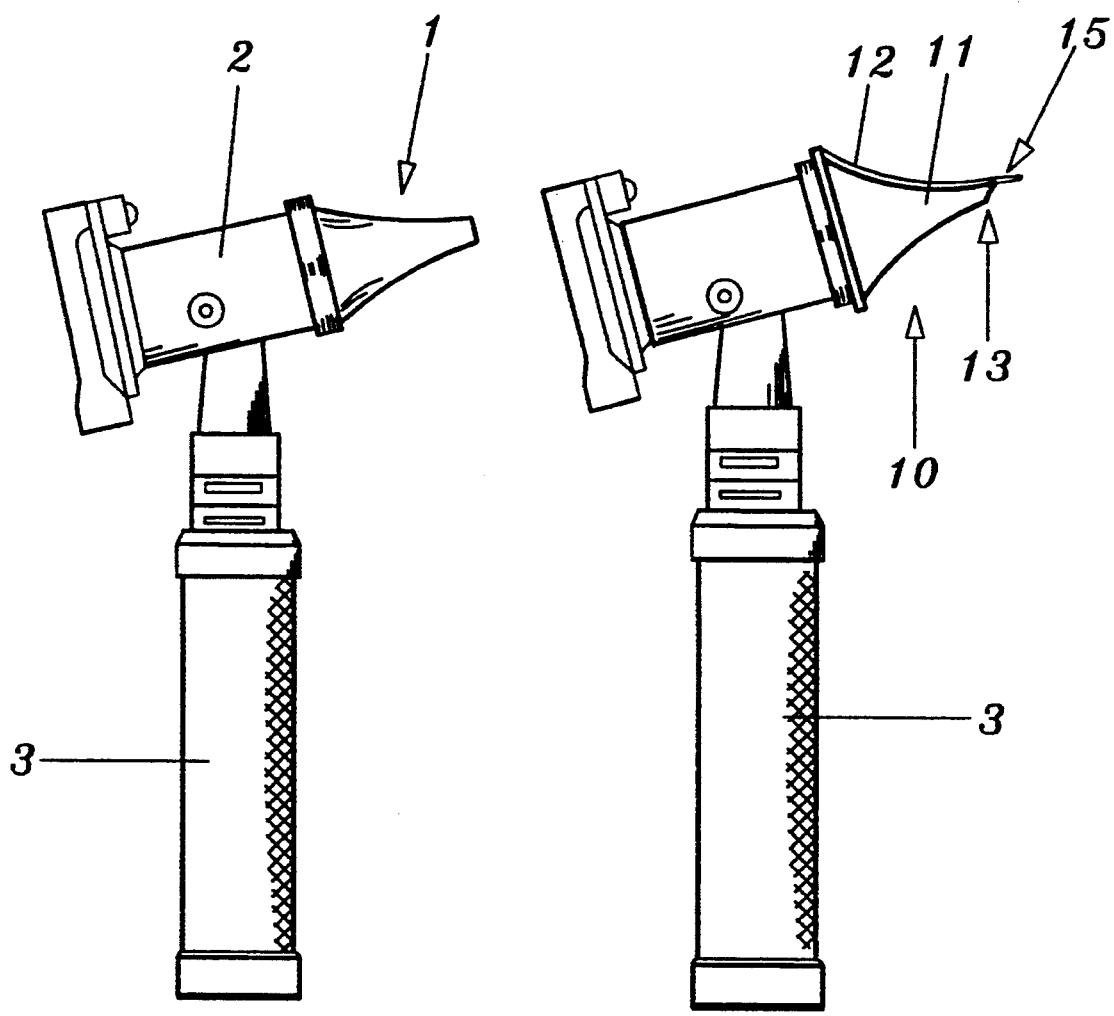
FIG. 1 is a side view of prior art otoscope with a conventional ear speculum.
FIG. 2 is a side view of an otoscope with an improved ear speculum.

Referring first to FIG. 1 a prior art ear speculum 1 is attached to a diagnostic otoscope 2. The otoscope 2 is attached to a handle 3 as is disclosed in U.S. Pat. No. 4,006,738, issued Feb. 8, 1977 to Moore.

In FIG. 2 an improved ear speculum 10 is attached to the otoscope 2. The improved speculum 10 has a conically shaped member 11 having a distal end 13. A shank 12 extends along the length of the conically shaped member 11. The curved distal end of the shank 15 forms a projection that extends approximately 5 to 8 mm from the distal end of the speculum 8. The curved distal end of the shank 15 is shown in a top plan view with a cutaway in FIG. 5. Movement of the curved distal end of the shank 15 is controlled with tensioning filaments 19 within peripheral channels 21. The channels 21 are located along peripheral edge of the narrow shank 12 and its distal end 15. The curved or convex nature of the distal end of the shank 15 facilitates resilience and bending. It presents a low profile for ease of insertion into orifices and allows bending in one direction only. The distal end of the speculum 13 has been shortened an equal 5 to 8 mm to maintain the same overall length of the speculum.

Figure 3:
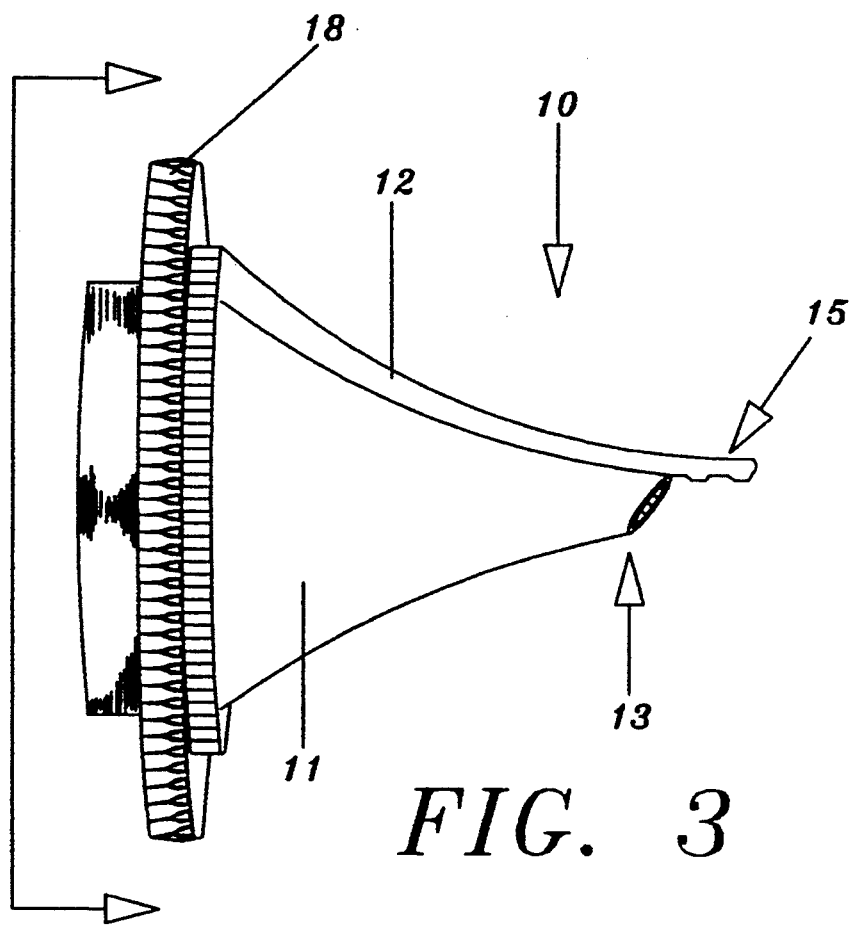
FIG. 3 is a side plan view of an improved ear speculum.

An enlarged view of an improved ear speculum 10 is shown in FIG. 3. The speculum 4 has a shank 12 along the length of the conically shaped member 11. The shank 12 extends beyond the distal end of the speculum 13. The curved distal end of the shank 15 is bendable and forms a curved bendable projection.

Again referring to FIG. 3 the distal end of the shank 15 can bend towards the distal end of the speculum 13. This movement is similar to a movable flap or finger. When bent back towards the distal end of the speculum 13, the curved distal end of the shank 15 will gather and hold materials such as ear wax or foreign objects. A rotatable knob 18 is shown adjacent to the viewing end 20 of the speculum.

Figure 4:
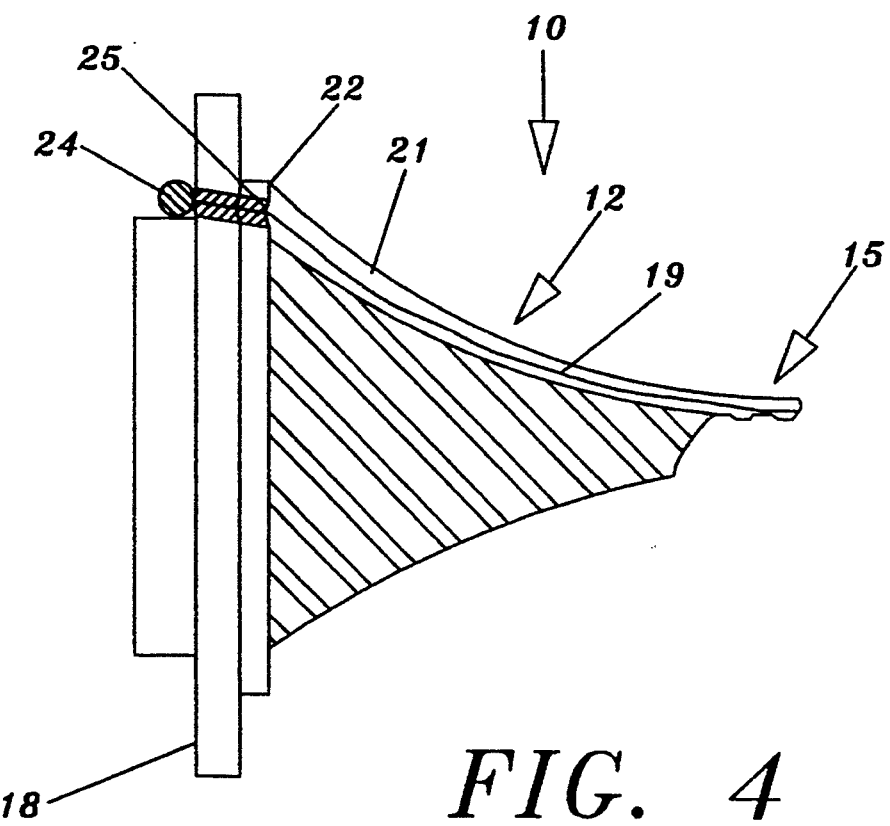
FIG. 4 is a longitudinal cross sectional view of the improved ear speculum as shown in FIG. 3.

A longitudinal cross section of the speculum 10 is presented in FIG. 4. Peripheral channels 21 exist within the shank 12. [These channels are similar to those within a common dual channeled swizzle stick or the spaces within tubes or arteries.]Tensioning filaments 19 can be made of monofilament thread, or surgical thread. They run through the peripheral channels 21. The filaments 19 are attached at one end to the distal end of the shank 15. The other end of the filaments is attached to the knob 18 near the proximal end of the shank 22 by means of hole 23 and knot 24. The distal end of the shank 15 is bent towards the distal end of the speculum 13 when the tensioning filaments 19 are pulled by rotating the knob 18.

Figure 5:
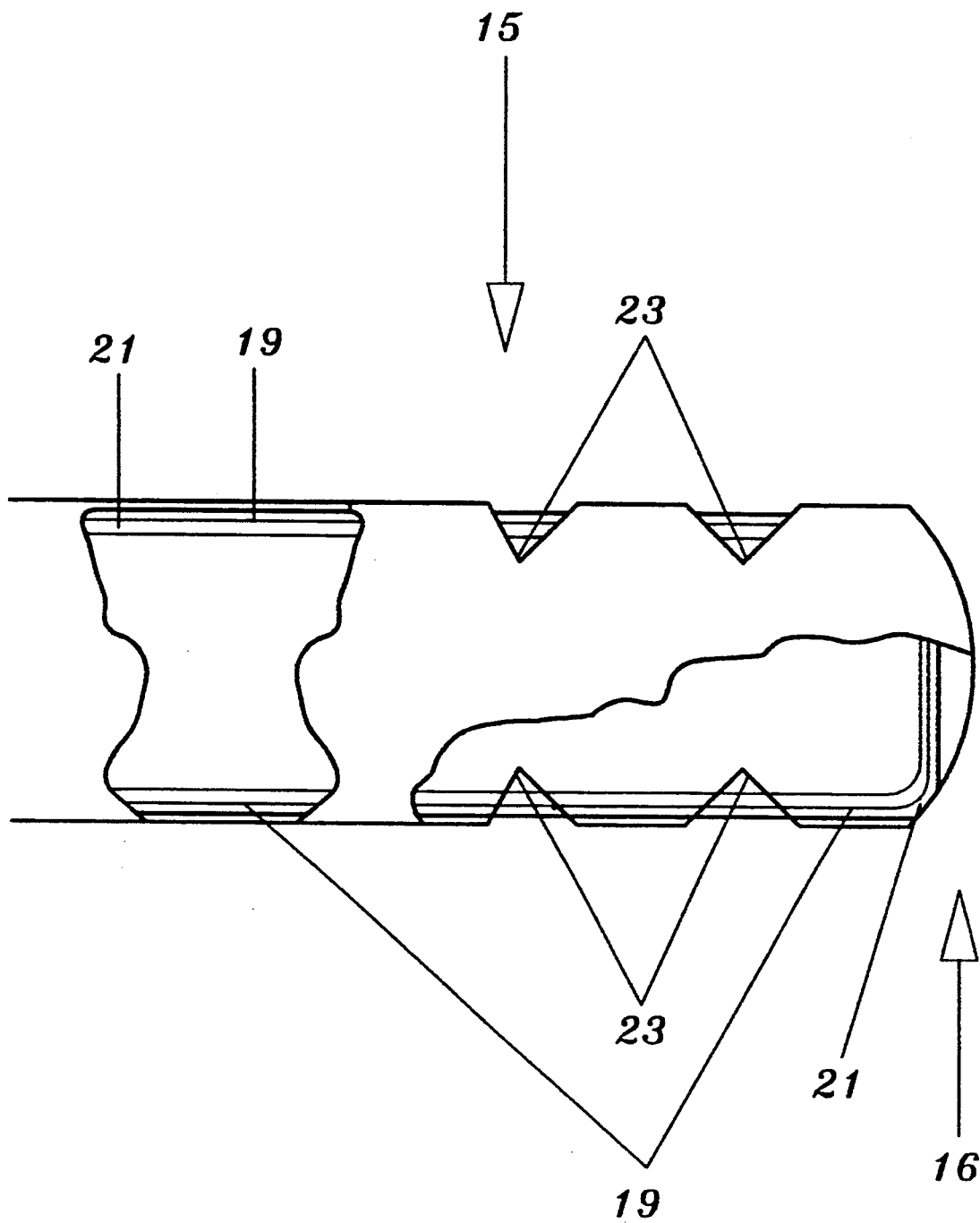
FIG. 5 is a top view of the distal end of the shank. Exposed segments are shown with partial cutaway cross-sectional views of the interior of the shank.

FIG. 5 is a partial cutaway of the distal end of the shank 15. Tensioning filaments 19 within peripheral channels 21 are attached to the distal end of the shank 15 at its tip 16. Peripheral notches 23 are located along the edges of the distal end of the shank 15 in order to facilitate bending.

Figure 6A:
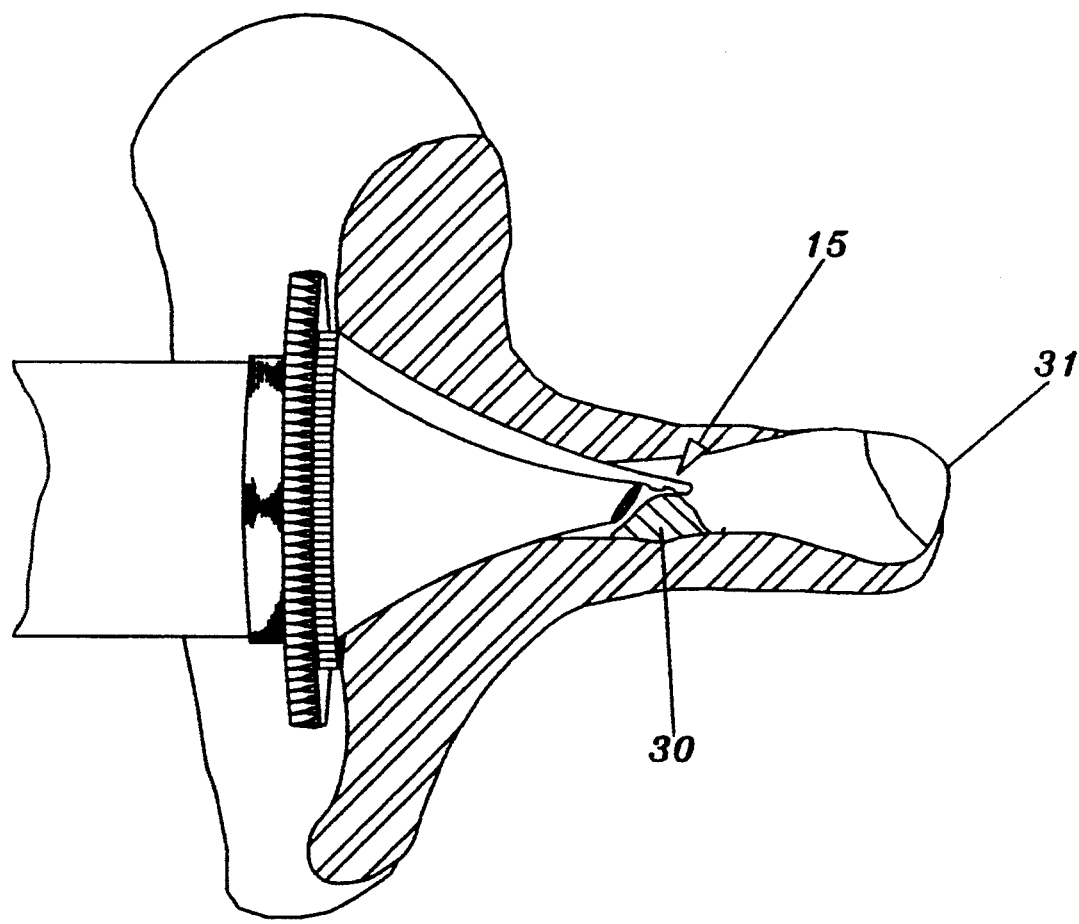
FIGS. 6(a) and (b) are side plan views of the improved speculum in operation, removing cerumen from an ear canal.
Figure 6B:
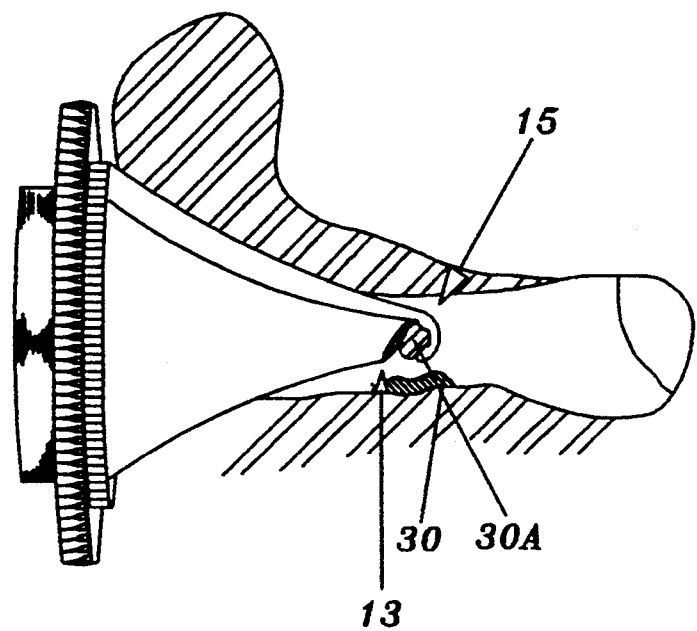

In FIG. 6(a) the distal end of the shank 15 is in an elongated position over an obstruction (possibly cerumen) 30 located next to an ear drum 31. In FIG. 6(b) the distal end of the shank 15 is bent towards the distal end of the speculum 13. The obstruction 30 has been extracted into obstruction 30A toward the distal end of the speculum 13 by the bent distal end of the shank 15.

Figure 7A:
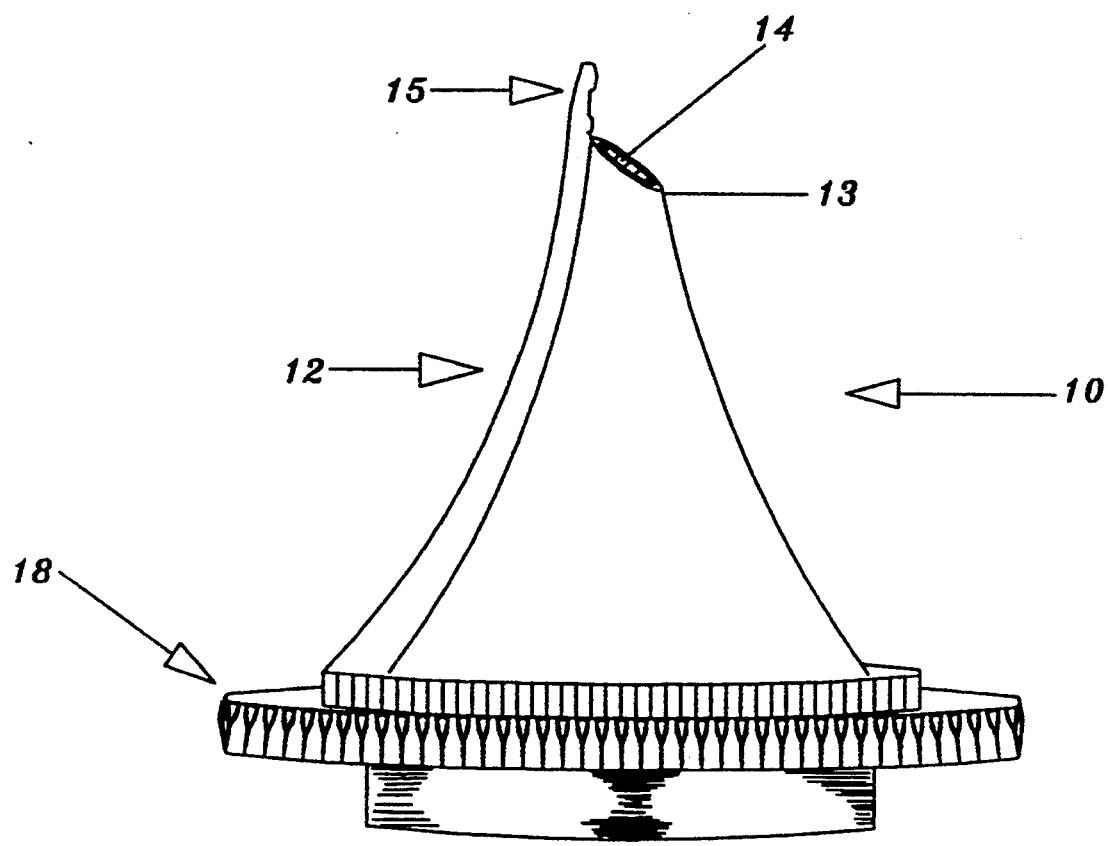
FIG. 7(a) is a side perspective view of an improved ear speculum.
Figure 7B:
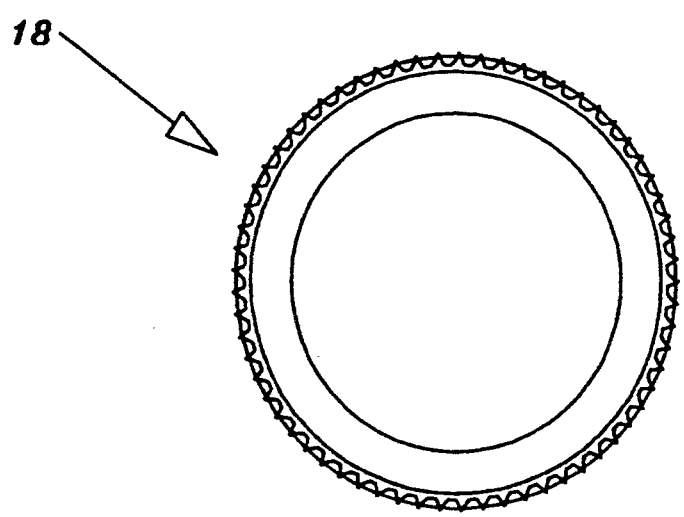
FIG. 7(b) is a top plan view of the rotatable knob of FIG. 7(a).

FIG. 7(a) is a side perspective view of the improved speculum 10. The shank 12 extends beyond the distal end of the speculum 14. The distal end 15 of the shank 12 is bendable under the control of the rotatable knob 18. The size and shape of the opening 14 may be modified to approximate the size and shape of the distal end of the shank 15 in its bent position. The rotatable knob 18 is also shown in a top plan view separated from the speculum 10 in FIG. 7(b).

Figure 8A:
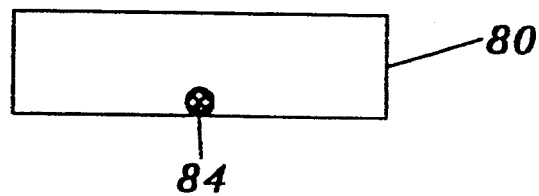
FIG. 8(a) is a cross sectional view of a flat shank having a single tensioning filament.
Figure 8B:
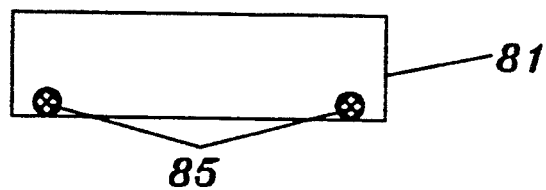
FIG. 8(b) is a cross sectional view of a flat shank having a pair of tensioning filaments, one on each side.
Figure 8C:
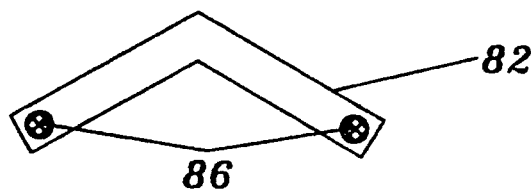
FIG. 8(c) is a cross sectional view of a V-shaped shank having a pair of tensioning filaments, one on each side.
Figure 8D:
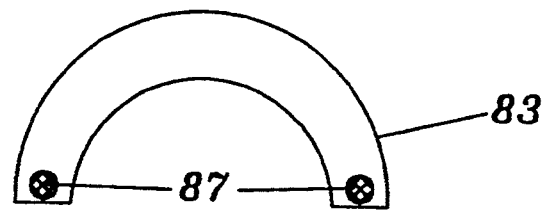
FIG. 8(d) is a cross sectional view of a convex shank having a pair of tensioning filaments, one on each side.

Referring next to FIG. 8(a) a bendable shank 80 is flat and has a single tensioning filament 84. In FIG. 8(b) a flat bendable shank 81 has a pair of tensioning filaments 85 along the peripheral edges. In FIG. 8(c) a triangular bendable shank 82 has a pair of tensioning filaments 86 along the peripheral edges. In FIG. 8(d) a convex bendable shank 83 has a pair of tensioning filaments 87 along the peripheral edges. It should be noted that the bending tension provided by the filaments is off the central longitudinal axis of the shank.

Figure 9:
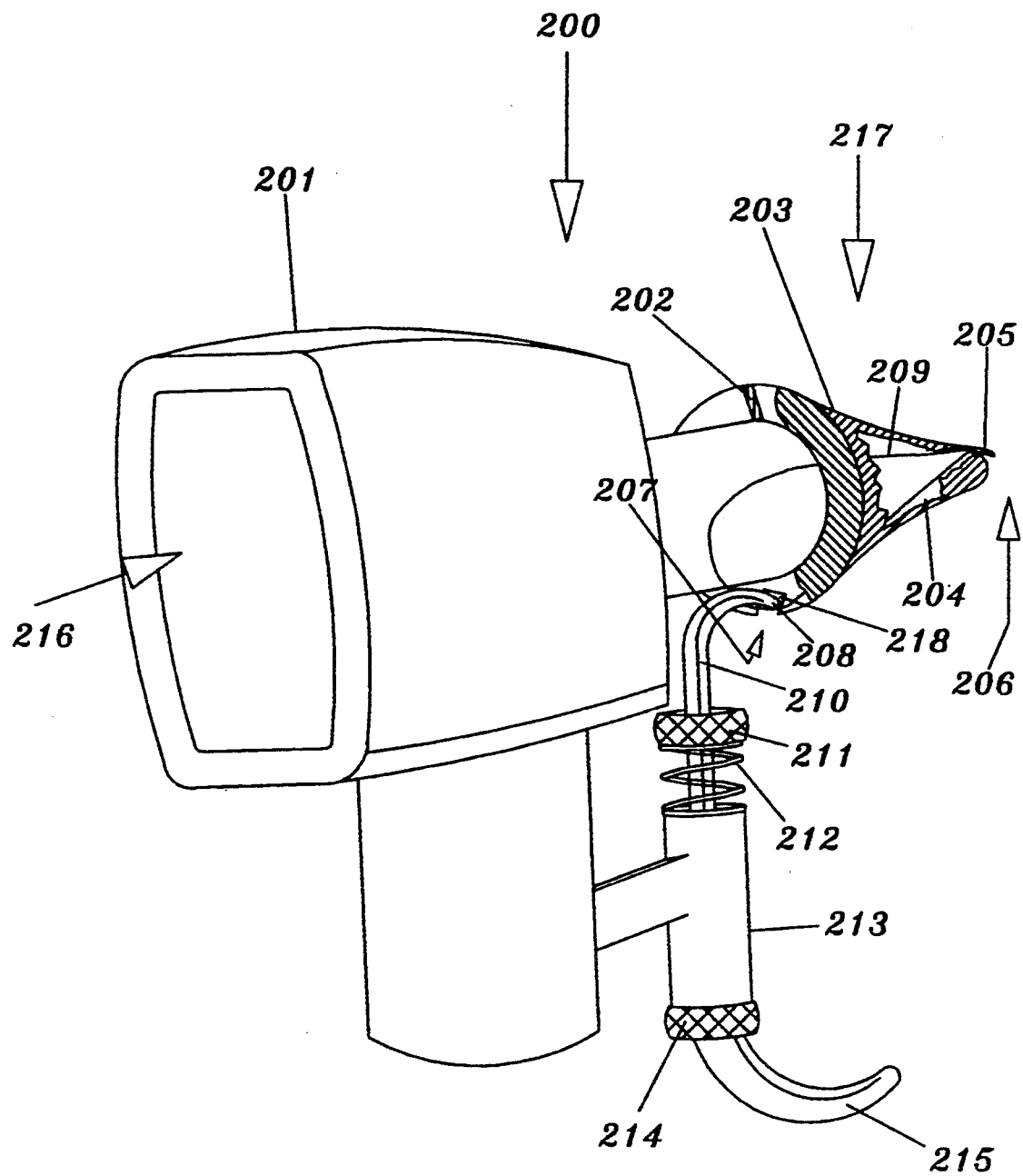
FIG. 9 is a side perspective view of an otoscope having a trigger mechanism to activate a disposable speculum having a bendable protrusion.

Referring next to FIG. 9 an improved diagnostic otoscope 200 has a viewing end (proximal end) 216. The otoscopic head 201 supports a disposable speculum 217. The disposable speculum 217 attaches to the otoscopic head 201 by means of an interlocking groove 202. The conically shaped member 203 has a filament conduit 204. A tensioning filament 209 slides inside the filament conduit 204. The tensioning filament 209 forms a filament loop 207.

A trigger assembly hook 208 grabs the filament loop 207 when the trigger 215 is pulled. When the filament loop 207 is pulled, the distal end 206 of the curved narrow protrusion 205 bends.

The trigger 215 is supported by a trigger assembly support 213 which slidably holds the hook shaft 210. The stops 211, 214 can be adjusted to provide the desired trigger stroke. The spring 212 returns the trigger to the unactuated position. The peripheral cutout 218 provides access for the trigger assembly hook 208 to reach the filament loop 207.

Figure 10:
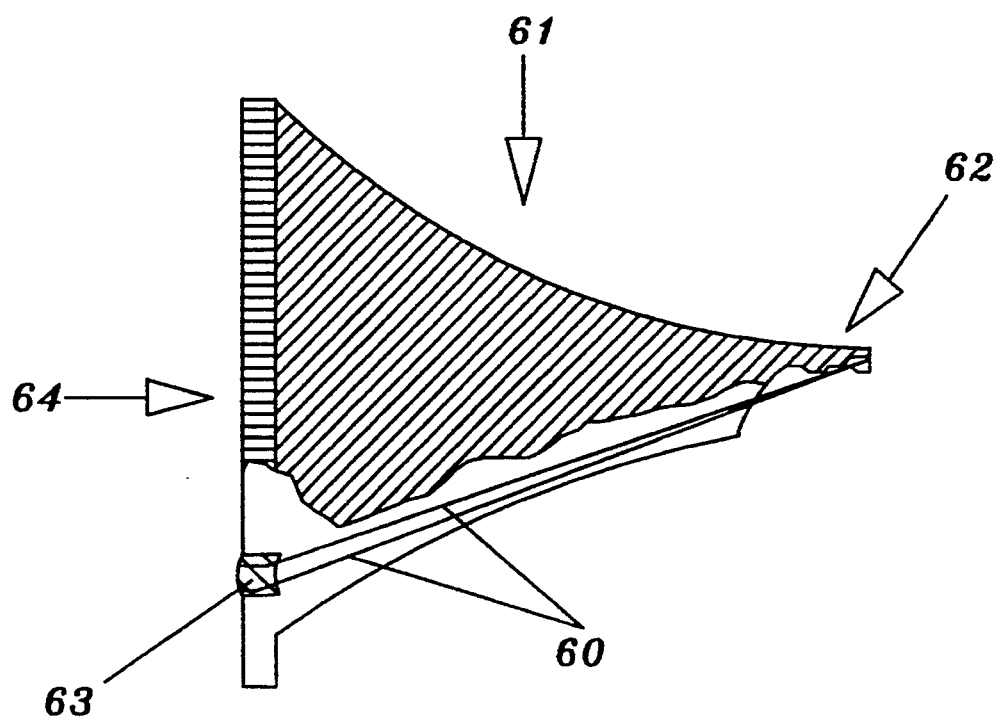
FIG. 10 is a longitudinal cross sectional view of an improved ear speculum having a direct pull means on the protrusion tip.

In FIG. 10 tensioning filaments 60 are placed within an improved speculum 61. The tensioning filaments 60 are attached at opposite sides of the distal end of a projection 62. The other end of the tensioning filaments 60 pass through an opening 63 in the base of the speculum near the viewing end 64 of the speculum 61. There are no peripheral channels on the projection through which the wires pass.

Figure 11:
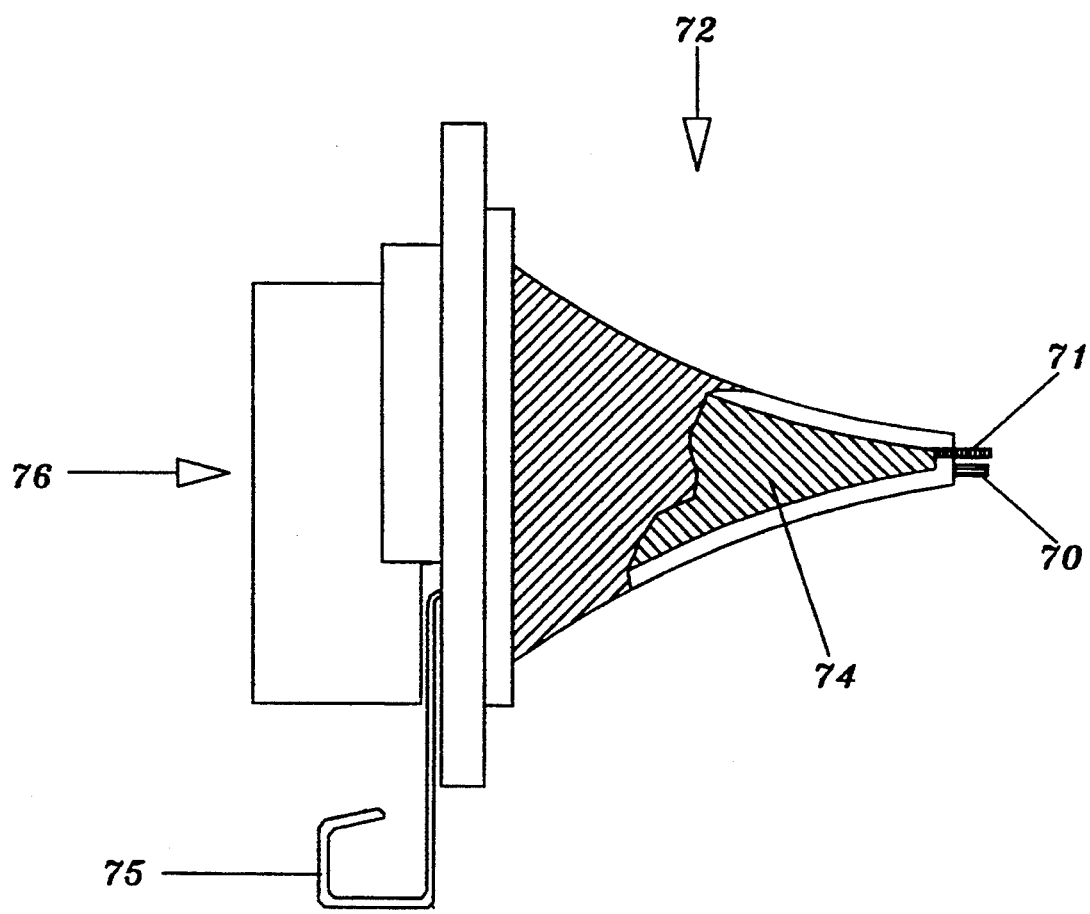
FIG. 11 is a side plan view with a partial cutaway of an improved ear speculum with cooperating immovable and rotatable spoon halves.

In FIG. 11 an immovable spoon half 70 and a rotatable spoon half 71 are seen in a cross section of an improved speculum 72. The rotatable spoon half 71 is rotatably mounted within the speculum 72 using an internal cone 74 slidingly engaged inside the speculum 72. The viewing end 76 of the speculum has a handle 75 to rotate the internal cone 74. Spoon halves 70,71 may meet or overlap when brought together.

Figure 12:
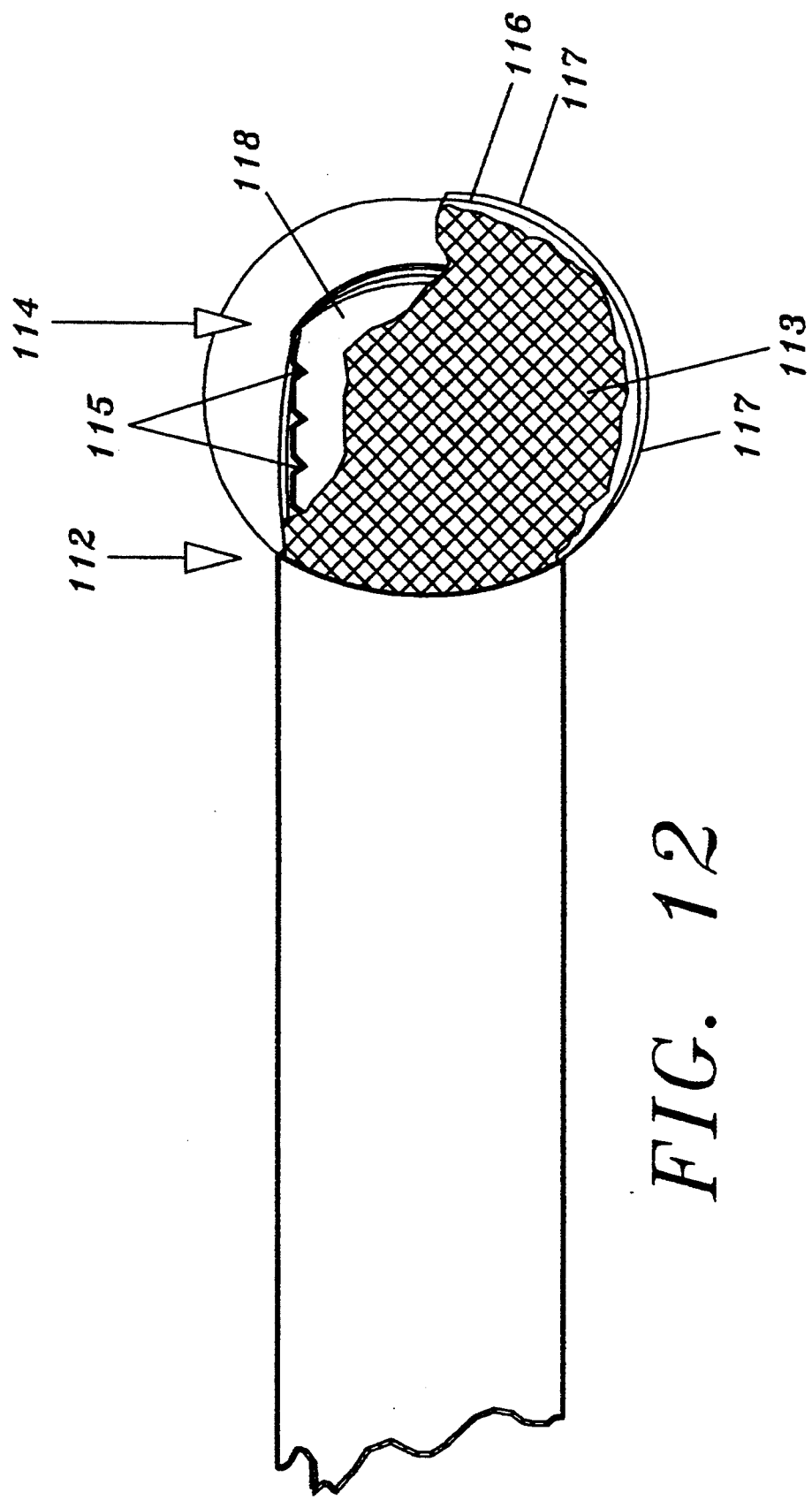
FIG. 12 is a top plan view of a surgical tool with a partial cutaway of a closable membrane member.

In FIG. 12 a top plan view of a surgical tool 112 is shown. A membrane 113 covers the entire convex top of the distal end of the shank 114 and its peripheral notches 115. A tensioning filament 116 is attached to membrane 113 along the peripheral edges of the membrane 117 which extend beyond the edges of the shank 118, thereby forming a bag. In operation the distal end of the shank 114 is passed beyond a foreign object (not shown). Then the tensioning filament 116 closes the membrane 113 around the foreign object for removal.

Figure 13:
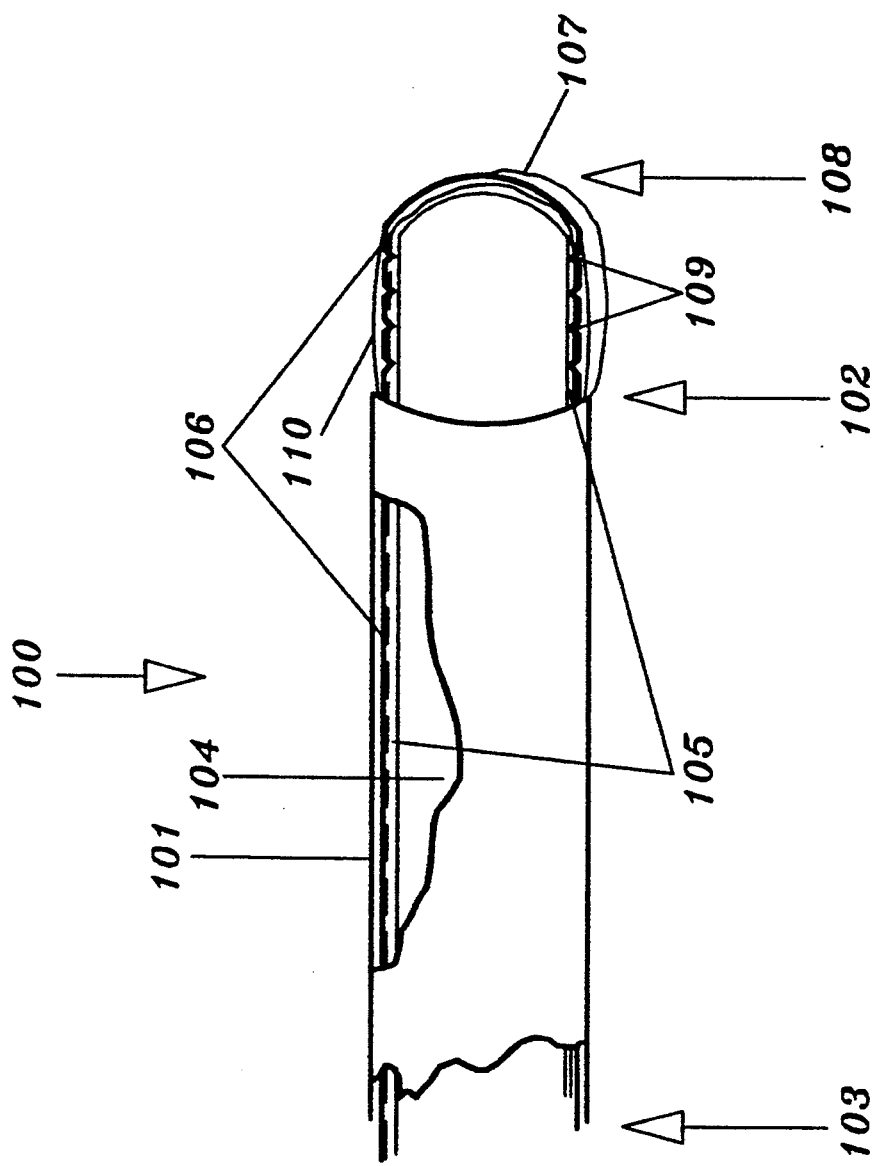
FIG. 13 is a top plan view of a surgical tool.

Referring next to FIG. 13 a surgical tool 100 has a cylindrical tube 101 with a distal end 102 and a proximal end 103. A shank 104 extends distally from inside the cylindrical tube 101. Channels 105 are located along the peripheral edges of the shank 104. A tensioning filament 106 runs through the channels 105 and around the distal end of the shank 108. A second tensioning filament 107 may be attached to the distal end of the shank 108. The second filament 107 does not run through the channels 105, but is threaded through the cylindrical tube 101. It pulls directly down on the distal end of the shank 108. To aid bending peripheral notches 109 are located on the edges of the distal end of the shank 108. A covering membrane 110 may be applied over the outer surface of the peripheral notches 109. The membrane 110 is used to protect delicate tissue and help contain debris or ear wax removed by the distal end of the shank 108.

Figure 14:
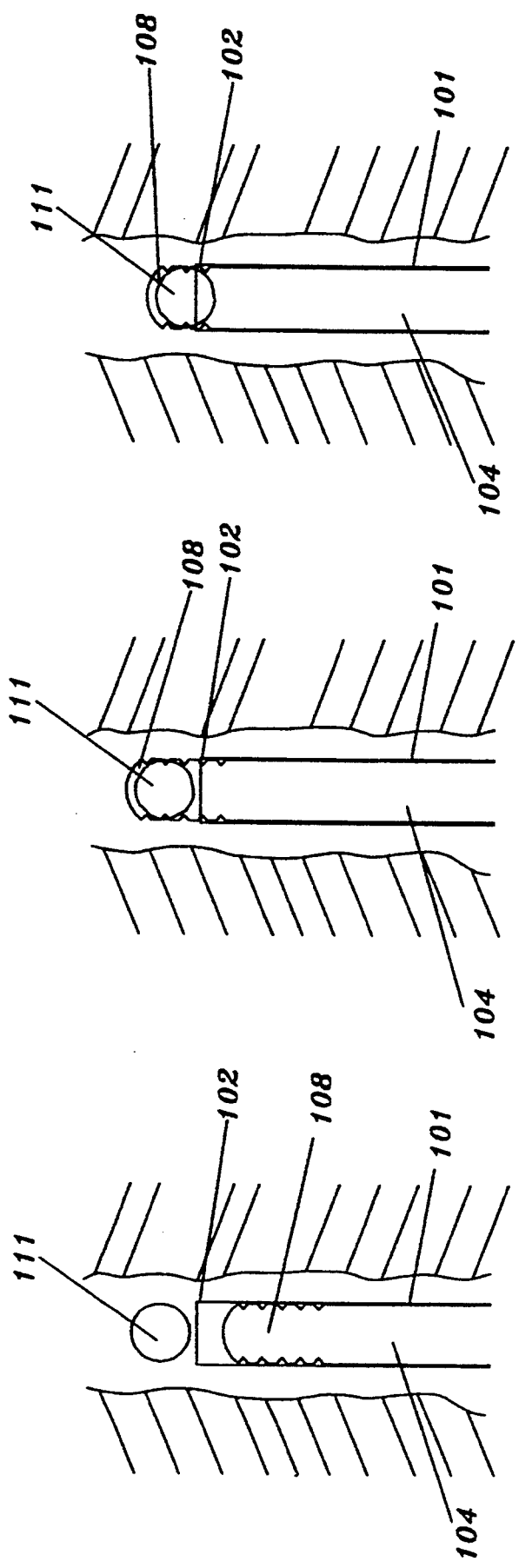
FIGS. 14(a),(b), and (c) are sequential top plan views of the surgical tool shown in FIG. 13.
FIG. 14(b) shows the distal end of the shank extended beyond the end of the cylindrical tube.
FIG. 14(c) shows a foreign object captured by the distal end of the shank.

Referring next to FIG. 14(a) the distal end 108 of the shank 104 (from FIG. 13) is in an elongated position while lying completely within the cylindrical tube 101. In FIG. 14(b) the distal end 108 of the shank 104 has been pushed past the distal end of the cylindrical tube 102 and over a foreign object 111. In FIG. 14c the foreign object 111 has been captured by activating the distal end 108 of the shank 104 to bend. The shank 104 is being retracted into the cylindrical tube 101.

Figure 15:
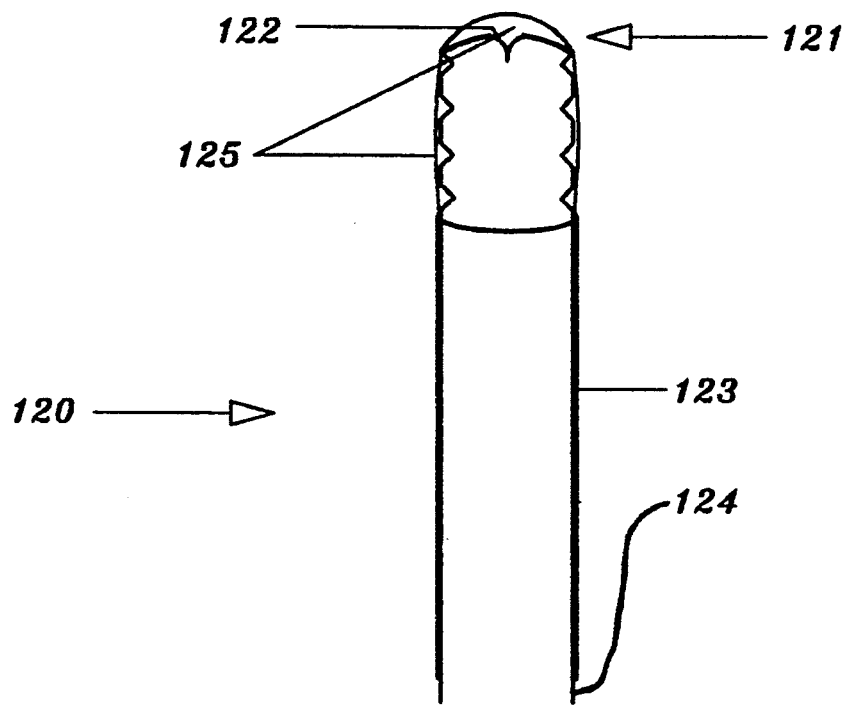
FIG. 15 is a top plan view of the tip of the distal end of the shank protruding from the surgical tool. A cutting blade is attached to the tip of the distal end of the shank.

In FIG. 15 a surgical tool 120 has a cylindrical tube 123 containing a bendable shank 124. The distal end 121 of the narrow curved shank 124 is equipped with a cutting edge 122 and a protective sheath 125. The cylindrical tube 123 may also be equipped with a fiber optic viewing means (not shown). Means for attaching additional tools may also be included within the cylindrical tube 123.

Figure 16:
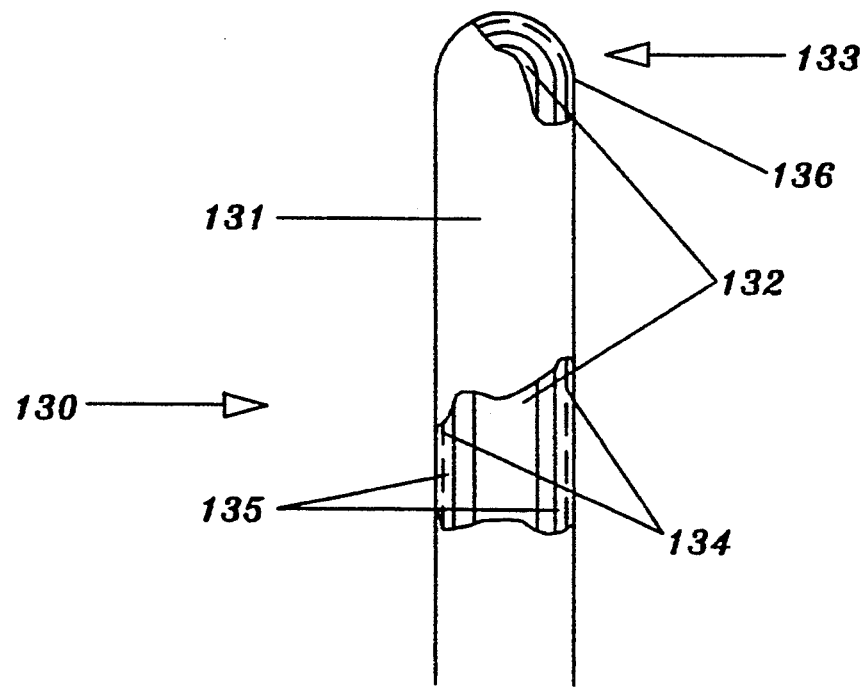
FIG. 16 is a top plan view with a partial cutaway of a hooded surgical tool.

In FIG. 16 a surgical tool 130 has a hood 131 affixed to the top of a shank 132. The distal end 133 of the shank 132 is bendable with or without the aid of peripheral notches (not shown). A tensioning filament 134 runs through channels 135 located along the peripheral edges 136 of the hood 131. The surgical tools 100, 120, 130 might be used in various medical procedures such as tissue or concretion removal, catherization, endoscopic, laproscopic and general surgical procedures. They might also be used outside of the medical field. The improved ear speculums 10,42,61,72,82,94 and surgical tools 100, 120, 130 might be either disposable or reusable.

Figure 17:
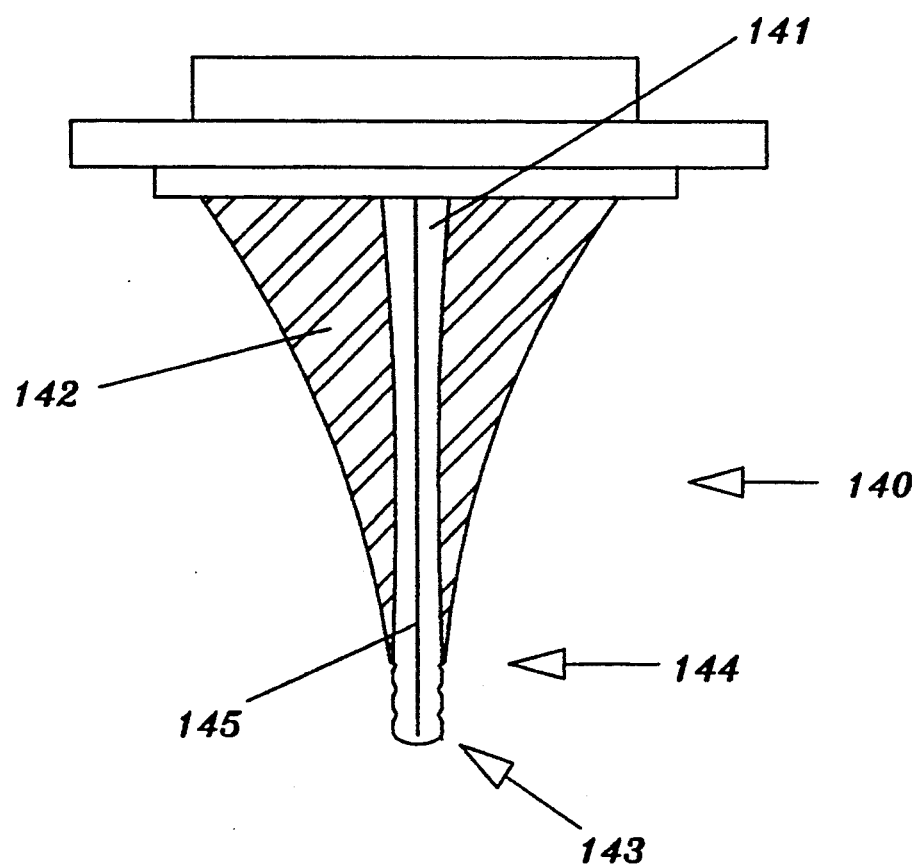
FIG. 17 is a top plan view of an improved ear speculum having a bendable protrusion activated by a single filament.

In FIG. 17 an improved ear speculum 140 is shown in a top plan view as having a single channeled narrow shank 141. The shank 141 extends along the length of the conically shaped member 142. The curved distal end of the shank 143 extends past the distal end of the speculum 144. Movement of the curved distal end of the shank 143 is controlled with a single tensioning filament 145. The tensioning filament 145 runs through the channel 146 of the single channeled shank 141.

Figure 18A:
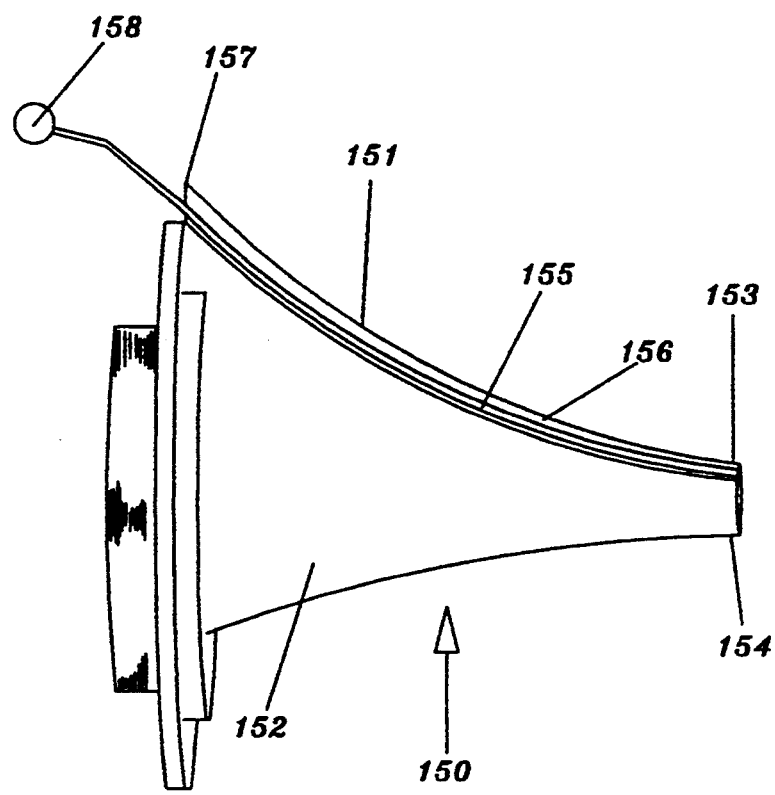
FIGS. 18(a), 18(b) are side cross sectional views of an improved ear speculum having a sliding prestressed protrusion.
Figure 18B:
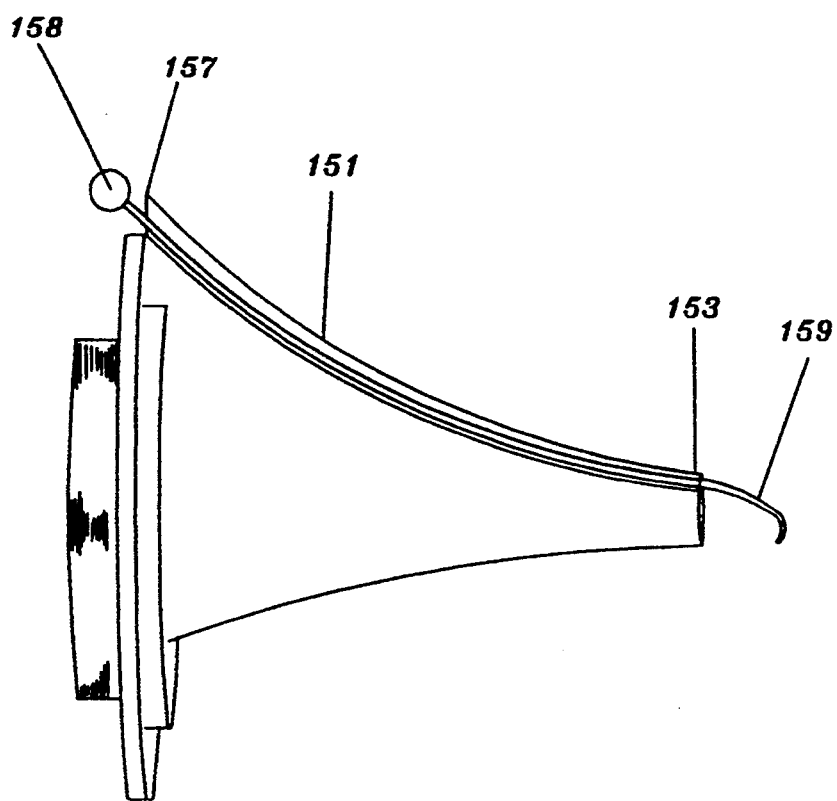

In FIG. 18(*a*) an improved ear speculum 150 is shown in a side cross sectional view as having a single channeled narrow shank 151. The shank 151 extends along the length of the conically shaped member 152. The distal end of the shank 153 is even with the distal end of the speculum 154. A prestressed member 155 runs through the channel 156 of the single channeled shank 151. The prestressed member 155 extends beyond the proximal end of the shank 157. A knob 158 is located on the proximal end of the prestressed member. The distal end of the prestressed member 159 can be housed completely within the distal end of the shank 153.

In FIG. 18(*b*) the distal end of the prestressed member 159 has been pushed outside of the distal end of the shank 153 by pushing the knob 158 towards the proximal end of the shank 157. Due to prestressing the distal end of the prestressed member 159 forms a curved projection when pushed outside of the distal end of the shank 153.

Figure 19:
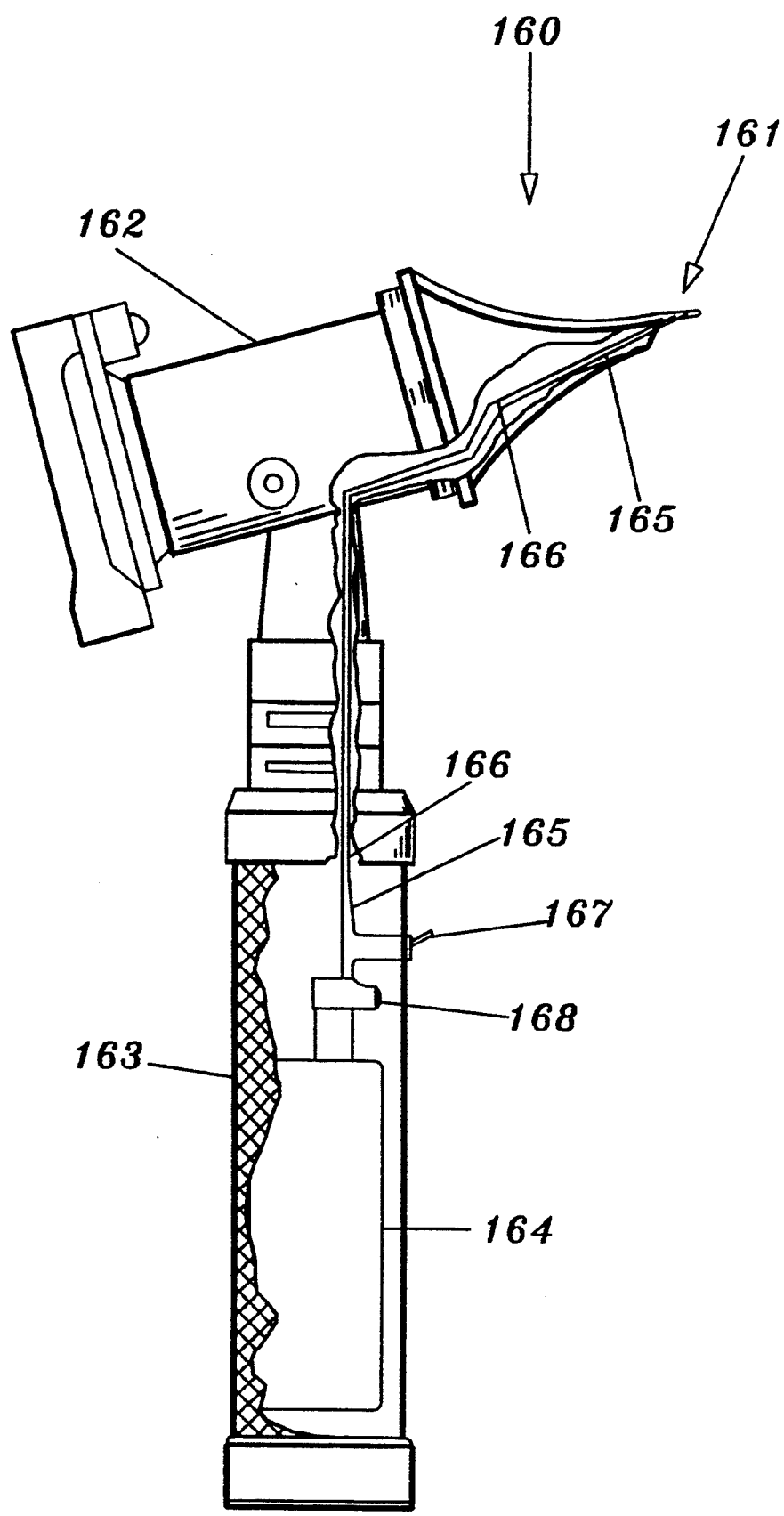
FIG. 19 is a side plan view with a partial cutaway of an otoscope. The protrusion is an electric shape-memory-effect-alloy.

A further embodiment is shown in FIG. 19. Another improved ear speculum 160 is pictured with a projection 161. The speculum 160 is attached to an otoscope 162 having a handle 163 and a power supply 164. The projection 161 comprises a shape-memory-effect alloy such as that described in U.S. Pat. No. 5,133,721 issued to Angulo on Jul. 28, 1992 and incorporated herein by reference. Two wires 165 and 166 extend from the projection 161. One strand of wire is connected to an on-off switch 167 and the other strand 166 is connected to a current limiting circuit 168. The current limiting circuit 168 is connected to the power supply 164. When the switch 167 is turned on the current causes the projection 161 to bend in the desired direction. Straightening the wires 165, 166 requires manual bending. It would be obvious to one skilled in the art to use the power supply for powering a light source.

Figure 20:
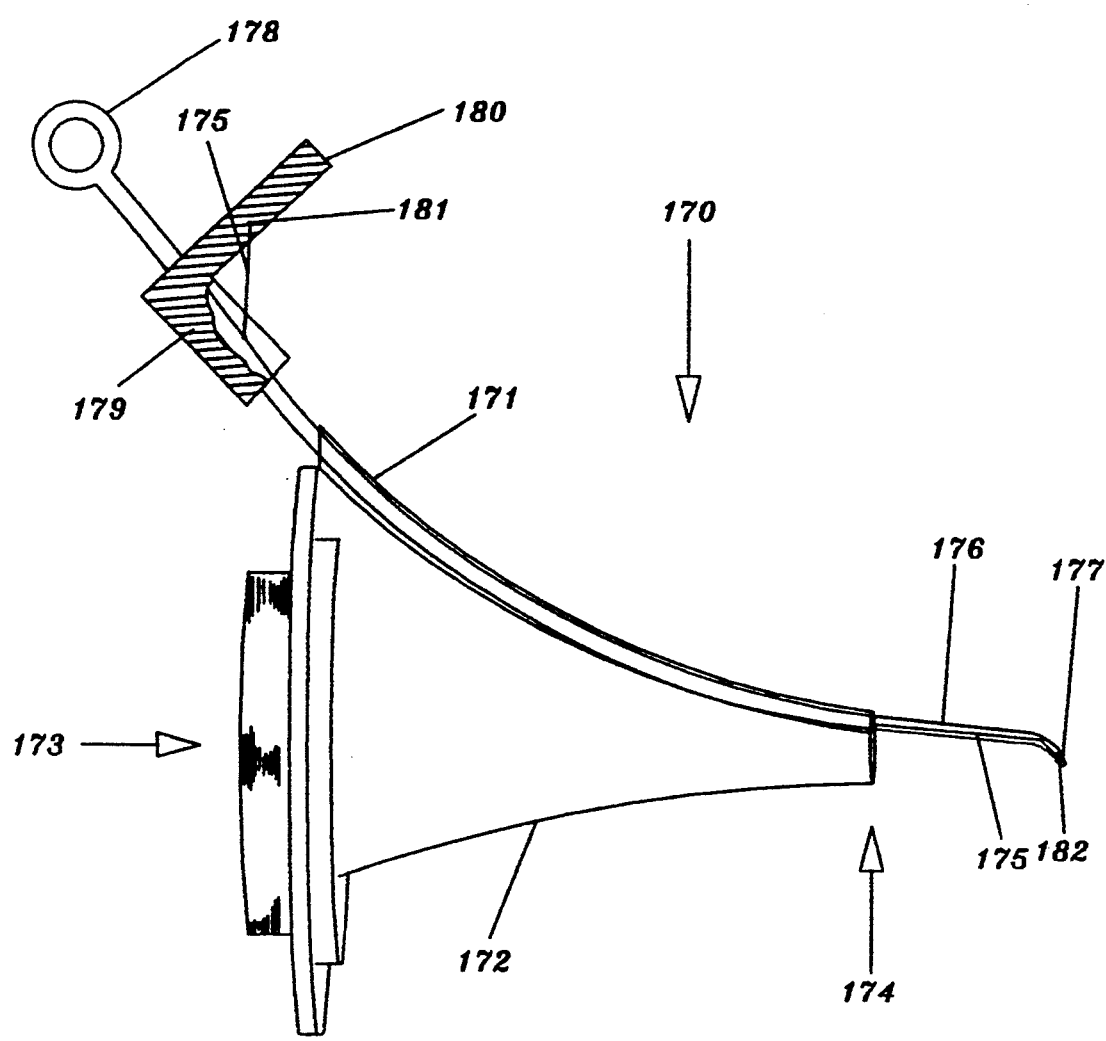
FIG. 20 is a side cross sectional view of an extendable embodiment of a bending protrusion on an ear speculum.

Referring next to FIG. 20 an improved nasal speculum 170 is shown in a cross sectional view. The conically shaped member 172 has a viewing (proximal) end 173 and a distal end 174. A cylindrical tube 171 is mounted on the top surface of the conically shaped member 172. Slidably engaged inside the cylindrical tube 171 is a narrow curved shank 176. A tensioning filament(s) 175 is contained in a longitudinal sleeve(s) 182 in a similar manner as shown in FIGS. 4, 5, 17. The distal end 177 of the narrow curved shank 176 is bent by means of pulling the tensioning control handle 179 away from the distal end 177. The tensioning filament(s) 175 is attached to the tensioning control handle 179 on the filament mount 180 at point 181. The narrow curved shank 176 can be extended and retracted to the desired length by pulling and/or pushing on the extension control handle 178.

A key is provided to facilitate review of the figures. The key matches component numbers with component descriptions.

KEY

1. Ear speculum
2. Otoscope head
3. Handle
10. Improved ear speculum
11. Conically shaped member
12. Narrow shank
13. Distal end of speculum
14. Opening in distal end of speculum
15. Distal end of narrow shank
16. Shank tip
17*b,c,d*. Cutting blades
18. Rotatable knob
19. Filament
20. Viewing end of speculum
21. Peripheral channels
22. Proximal end of shank
23. Peripheral notches on shank
24. Hole
25. Knot
30. Foreign object or ear wax
31. Ear drum
60. Tensioning filaments
61. Improved speculum
62. Distal end of a projection
63. Opening in base of speculum
64. Viewing end of speculum
70. Immovable spoon half
71. Rotatable spoon half
72. Improved speculum
73. Second rotatable spoon half
74. Internal cone
75. Handle
76. Viewing end of speculum
80,81,82,83. Bendable shank
84,85,86,87. Tensioning filaments
100. Surgical tool
101. Cylindrical tube
102. Distal end of cylindrical tube
103. Proximal end of cylindrical tube
104. Shank within cylindrical tube
105. Narrow shank peripheral channels
106. Tensioning filament
107. Second tensioning filament
108. Distal end of shank
109. Peripheral notches
110. Covering membrane
111. Foreign object
112. Surgical tool
113. Membrane
114. Distal end of the shank
115. Peripheral notches
116. Tensioning filament
117. Peripheral edges of the membrane
118. Shank
120. Surgical tool
121. Distal end of the shank
122. Cutting edge
123. Cylindrical tube
124. Narrow curved shank
125. Protective sheath
130. Surgical tool
131. Hood
132. Narrow shank
133. Distal end of shank
134. Tensioning filament
135. Channels
136. Peripheral edges of flexible material
140. Improved ear speculum
141. Single channeled narrow shank
142. Conically shaped member
143. Curved distal end of the shank
144. Distal end of the speculum
145. Tensioning filament
146. Channel in narrow shank
150. Improved ear speculum 151. Single channeled narrow shank
152. Conically shaped member
153. Distal end of the shank
154. Distal end of the speculum
155. Prestressed member
156. Channel
157. Proximal end of the shank
158. Knob
159. Distal end of the prestressed member
160. Improved ear speculum
161. Projection
162. Otoscope
163. Handle
164. Power supply
165. Wire
166. Wire
167. On-off switch
168. Current limiting circuit
170. Improved ear speculum
171. Cylindrical tube
172. Conically shaped member
173. Viewing (proximal) end of the improved ear speculum
174. Distal end
175. Tensioning filament
176. Narrow curved shank
177. Distal end of the narrow curved shank
178. Extension control handle
179. Tensioning control handle
180. Filament mount for the tensioning control handle
181. Filament attachment point
182. Longitudinal sleeve
200. Improved otoscope and ear speculum
201. Otoscopic head
202. Interlocking groove
203. Conically shaped member
204. Filament conduit
205. Curved narrow protrusion
206. Distal end of curved narrow protrusion
207. Filament loop
208. Trigger assembly hook
209. Tensioning filament
210. Hook shaft
211. Stop
212. Spring
213. Trigger assembly support
214. Stop
215. Trigger
216. Viewing end (proximal)
217. Disposable speculum
218. Peripheral cutout Although the present invention has been described with reference to preferred embodiments, numerous modifications and variations can be made and still the result will come within the scope of the invention. No limitation with respect to the specific embodiments disclosed herein is intended or should be inferred.

I claim:

1. An ear speculum for viewing an obstruction in an ear canal, the ear speculum comprising a substantially conically shaped member having a truncated distal end suitable for entering the ear canal and a proximal end for viewing, the ear speculum further comprising;

a shank extending distally from said distal end;

said shank further comprising a distal and a proximal end;

said shank further comprising a channel means running lengthwise;

a tensioning filament running continuously through said channel means;

said tensioning filament further comprising means for pulling at the proximal end of said ear speculum, wherein said shank may be inserted in the ear canal past said obstruction, and said means for pulling may be activated, thereby bending said shank at its distal end thus enabling extraction of the obstruction without exerting any off axial or rotational forces on the ear canal.

2. The ear speculum of claim 1 wherein said shank further comprises peripheral notches to further enable bending.

3. The ear speculum of claim 1 wherein said means for pulling further comprises a knob adjacent to said proximal end of said conically shaped member, and said tensioning filament is affixed thereto, wherein rotating said knob pulls said tensioning filament.

4. The ear speculum of claim 1 wherein said means for pulling further comprises a trigger, and said tensioning filament is affixed thereto, wherein pulling said trigger pulls said tensioning filament.

5. The ear speculum of claim 1 wherein said conically shaped member further comprises attachment means attaching said ear speculum to an otoscope.

6. The ear speculum of claim 5 wherein said otoscope further comprises a trigger assembly having means for engaging said tensioning filament.

7. The ear speculum of claim 6 wherein said means for engaging further comprises said tensioning filament having a loop and said trigger assembly having a hook engaged with said loop.

8. The ear speculum of claim 1 wherein said channel means further comprises a central longitudinal channel in the shank.

9. The ear speculum of claim 1 wherein said channel means further comprises a pair of peripheral channels running longitudinally along the shank.

10. The ear speculum of claim 1 wherein said shank further comprises an axial curve shape.

11. A nasal speculum for viewing an obstruction in a nasal passage, the nasal speculum comprising a substantially conically shaped member having a truncated distal end suitable for entering the nasal passage, and a proximal end for viewing, the nasal speculum further comprising:

a channel running longitudinally along the outside of the conically shaped member and ending at the distal end of the conically shaped member;

a shank slidingly engaged in the channel; means to extend and retract the shank from the distal end of the channel;

said shank further comprising a distal and a proximal end;

said shank further comprising a channel means running lengthwise;

a tensioning filament running continuously through said channel means;

said tensioning filament further comprising means for pulling at the proximal end of the nasal speculum, wherein said shank may be inserted in the nasal passage to a depth determined by the means to extend and retract the shank, and a foreign object can be extracted by activating said means for pulling at the proximal end of the speculum thereby bending said shank at its distal end without exerting any off axial or rotational forces on said nasal passage.

* * * * *